United States Patent [19]

Jung

[11] Patent Number: 5,444,057
[45] Date of Patent: Aug. 22, 1995

[54] CARBAPENEM-ANTIBIOTIC COMPOUNDS

[75] Inventor: Frederic H. Jung, Rilly La Montagne, France

[73] Assignee: Zeneca Limited, London, England

[21] Appl. No.: 309,594

[22] Filed: Sep. 15, 1994

Related U.S. Application Data

[63] Continuation of Ser. No. 86,835, Jul. 7, 1993, abandoned.

[30] Foreign Application Priority Data

Jul. 21, 1992 [EP] European Pat. Off. ........... 92402104

[51] Int. Cl.⁶ .................. A01N 43/00; A61K 31/395; C07D 487/04
[52] U.S. Cl. .................................... 514/210; 540/350; 540/200; 546/281
[58] Field of Search .................. 514/210; 540/350

[56] References Cited

U.S. PATENT DOCUMENTS

| | | |
|---|---|---|
| 4,206,219 | 6/1980 | Christensen et al. . |
| 4,208,422 | 6/1980 | Christensen et al. . |
| 4,218,462 | 8/1980 | Christensen et al. . |
| 4,232,036 | 11/1980 | Christensen et al. . |
| 4,925,838 | 5/1990 | Murata ............... 540/350 |
| 4,933,333 | 6/1990 | Sunagawa et al. ............ 540/310 |
| 4,963,544 | 10/1990 | Murata et al. . |
| 5,194,624 | 3/1993 | Murata et al. . |
| 5,215,983 | 6/1993 | Murata et al. . |

FOREIGN PATENT DOCUMENTS

| | | |
|---|---|---|
| 0017992 | 10/1980 | European Pat. Off. . |
| 0126587 | 11/1984 | European Pat. Off. . |
| 0160391 | 11/1985 | European Pat. Off. . |
| 0182213 | 5/1986 | European Pat. Off. . |
| 0243686 | 11/1987 | European Pat. Off. . |
| 0442497 | 8/1991 | European Pat. Off. . |
| 0443883 | 8/1991 | European Pat. Off. . |
| 0472062 | 2/1992 | European Pat. Off. . |
| 17479 | 10/1992 | European Pat. Off. ............ 540/350 |
| 017480 | 10/1992 | European Pat. Off. ............ 540/350 |
| 60-233076 | 11/1985 | Japan . |
| 9217481 | 10/1992 | WIPO . |

*Primary Examiner*—Johann Richter
*Assistant Examiner*—Rebecca Cook
*Attorney, Agent, or Firm*—Cushman Darby & Cushman

[57] ABSTRACT

The present invention relates to carbapenems and provides a compound of the formula (I)

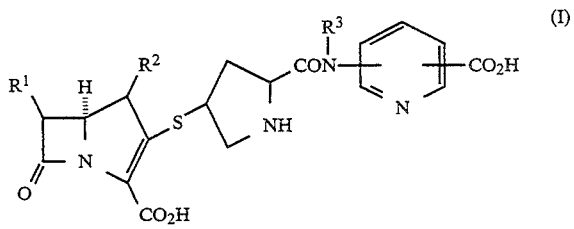

wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl;

and the pyridyl group is bonded to the nitrogen of the linking carbamoyl group by a carbon atom, is substituted with the carboxy group on a carbon atom and is optionally substituted on one or two pyridyl ring carbon atoms; or a pharmaceutically acceptable salt or in vivo hydrolyzable ester thereof. Processes for their preparation, intermediates in their preparation, their use as therapeutic agents and pharmaceutical compositions containing them.

8 Claims, No Drawings

CARBAPENEM-ANTIBIOTIC COMPOUNDS

This is a continuation of application Ser. No. 08/086,835, filed on Jul. 7, 1993, which was abandoned upon the filing hereof.

The present invention relates to carbapenems and in particular to such compounds containing a carboxy substituted pyridyl group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

European patent application, publication no. 0126587-A2 discloses thiopyrrolidinyl carbapenem compounds and includes specific compounds in which the pyrrolidine ring is substituted by pyridylcarbamoyl.

The present invention provides thiopyrrolidinyl carbapenem compounds wherein the pyrrolidine ring is substituted by a carboxypyridylcarbamoyl group. These compounds show a broad spectrum of antibacterial activity including both Gram positive and negative, aerobic and anaerobic bacteria. They exhibit good stability to beta-lactamases. In addition representative compounds of this invention exhibit favourable pharmacokinetics in particular long half life.

The carbapenem derivatives referred to herein are named in accordance with the generally accepted semi-systematic nomenclature:

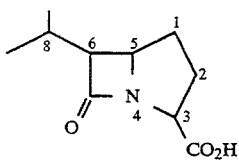

Accordingly the present invention provides a compound of the formula (I)

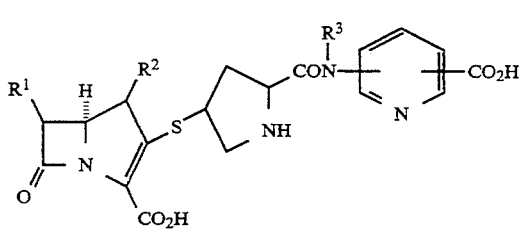

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl; and the pyridyl group is bonded to the nitrogen of the linking carbamoyl group by a carbon atom, is substituted with the carboxy group on a carbon atom, and is optionally further substituted, on ring carbon atoms, by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, $C_{1-4}$alkylS(O)$_n$- (wherein n is 0–2), $C_{1-4}$alkanoylamino, $C_{1-4}$alkanoyl(N-$C_{1-4}$alkyl)amino, carbamoyl, $C_{1-4}$alkylcarbamoyl and di-$C_{1-4}$alkylcarbamoyl:

or a pharmaceutically acceptable salt or in vivo hydrolysable ester thereof.

The term alkyl includes all straight and branched chain structures, for example, $C_{1-4}$alkyl includes n-butyl and 2-methylpropyl.

Preferably R is 1-hydroxyethyl.

$R^2$ is hydrogen or $C_{1-4}$alkyl for example methyl, ethyl, n-propyl, 1-methylethyl and -butyl.

Preferably $R^2$ is hydrogen or methyl and in particular $R^2$ is methyl.

$R^3$ is hydrogen or $C_{1-4}$alkyl for example methyl, ethyl, n-propyl, 1-methylethyl and n-butyl.

Preferably $R^3$ is hydrogen or methyl.

Most preferably $R^3$ is hydrogen.

Suitable substituents for the pyridyl ring include, for example:

| | |
|---|---|
| for halo: | fluoro, chloro and bromo; |
| for $C_{1-4}$alkyl: | methyl, ethyl, propyl, 1-methylethyl, butyl and 2-methylpropyl; |
| for $C_{1-4}$alkoxy: | methoxy, ethoxy, propoxy, 1-methylethoxy, butoxy and 2-methylpropoxy; |
| for $C_{1-4}$alkylcarbamoyl: | methylcarbamoyl, ethylcarbamoyl and propylcarbamoyl; |
| for di-$C_{1-4}$alkylcarbamoyl: | dimethylcarbamoyl and diethylcarbamoyl; |
| for $C_{1-4}$alkylamino: | methylamino, ethylamino and propylamino; |
| for di-$C_{1-4}$alkylamino: | dimethylamino, diethylamino and methylethylamino; |
| for $C_{1-4}$alkylS(O)$_n$-: | methylthio, methylsulfinyl and methylsulfonyl; |
| for $C_{1-4}$alkanoylamino: | acetamido and propionamido; |
| for $C_{1-4}$alkoxycarbonyl: | methoxycarbonyl and ethoxycarbonyl; |
| for $C_{1-4}$alkanoyl(N-$C_{1-4}$alkyl)amino: | N-methylacetamido and N-ethylacetamido. |

Preferably when the pyridyl ring is optionally substituted, the optional substituents are selected from halo, cyano, $C_{1-4}$alkyl, nitro, carboxy, hydroxy, $C_{1-4}$alkoxy, carbamoyl, amino and trifluoromethyl.

The present invention covers all epimeric, diastereoisomeric and tautomeric forms of the compounds of the formula (I) wherein the absolute stereochemistry at the 5-position is as illustrated in formula (I). When a bond is represented as a wedge, this indicates that in three dimensions the bond would be coming forward out of the paper and when a bond is represented as hatched, this indicates that in three dimensions the bond would be going back into the paper. The compounds of the formula (I) have a number of other centres of optical activity, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

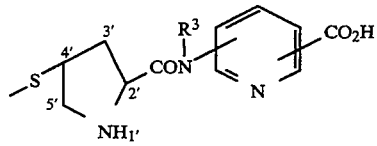
(II)

Preferred compounds are those in which the beta-lactam protons are in trans configuration with respect to one another. When R¹ is 1-hydroxyethyl or 1-fluoroethyl it is preferred that the 8-substituent has the R-configuration. Thus a preferred class of compounds is that of the formula (III):

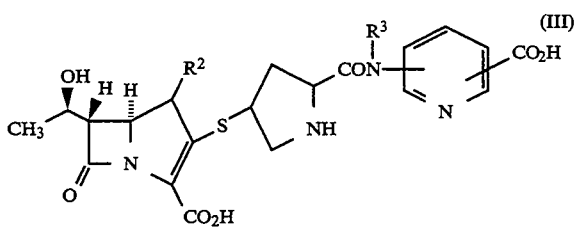
(III)

and pharmaceutically acceptable salts and in vivo hydrolysable esters thereof, wherein R² R³ and optional substituents on the pyridyl ring are as hereinbefore defined.

When R² is $C_{1-4}$alkyl for example methyl it is preferred that the compound is in the form of the 1R configuration.

In one aspect the pyrrolidine ring has the following absolute stereochemistry at the 2'- and 4'- positions:

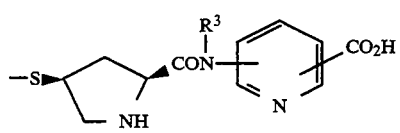

In another aspect the pyrrolidine ring has the following absolute stereochemistry at the 2' and 4' positions:

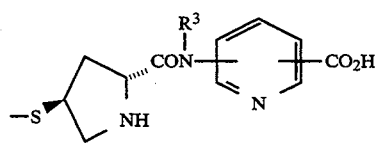

A suitable class of compounds of the present invention is that of the formula (IV):

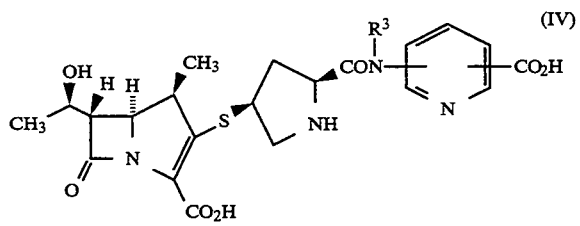
(IV)

and pharmaceutically acceptable salts and in vivo hydrolysable esters thereof; wherein R³ and optional substituents on the pyridyl ring are as defined hereinbefore in formula (I).

In another aspect a suitable class of compounds are the compounds of the formula (IVA):

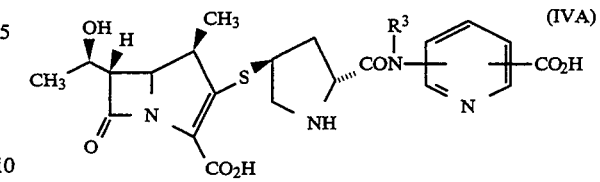
(IVA)

and pharmaceutically acceptable salts and in vivo hydrolysable esters thereof; wherein R³ and optional substituents on the pyridyl ring are as defined in formula (I).

In another aspect a suitable class of compounds are the compounds of the formula (IV) wherein R³ is hydrogen, methyl or ethyl; and optional substituents on the pyridyl ring are as defined hereinabove in formula (I).

In yet another aspect a suitable class of compounds is that of the compounds of the formula (IV) wherein the pyridyl ring is optionally further substituted by one or two substituents selected from methyl, ethyl, hydroxy, carboxy, cyano, fluoro, chloro, bromo, carbamoyl, nitro, methoxy, ethoxy and propoxy; and R³ is as defined hereinbefore in formula (I).

A particular class of compounds of the present invention is that of the formula (IV) wherein: R³ is hydrogen or methyl; and the pyridyl ring is optionally further substituted by one or two substituents selected from methyl, ethyl, hydroxy, carboxy, cyano, chloro, bromo, nitro, methoxy and ethoxy.

A particular class of compounds of the present invention is that of the formula (IVA) wherein: R³ is hydrogen or methyl; and the pyridyl ring is optionally further substituted by one or two substituents selected from methyl, ethyl, hydroxy, carboxy, cyano, chloro, bromo, nitro, methoxy and ethoxy.

A preferred class of compounds of the present invention is that of the formula (IV) wherein: R³ is hydrogen; and the pyridyl ring is optionally further substituted by one or two substituents selected from methyl, hydroxy, chloro and carboxy.

A preferred class of compounds of the present invention is that of the formula (IVA) wherein: R³ is hydrogen; and the pyridyl ring is optionally further substituted by one or two substituents selected from methyl, hydroxy, chloro and carboxy.

A more preferred class of compounds of the present invention is that of the formula (IV) wherein: R³ is hydrogen; and the pyridyl ring is not further substituted.

A more preferred class of compounds of the present invention is that of the formula (IVA) wherein: R³ is hydrogen; and the pyridyl ring is not further substituted.

Particular compounds of the present invention are, for example, the following compounds of the formula (IV):

(1R,5S,6S,8R,2'S,4'S)-2-(2-(4-carboxy-2-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-5-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6-pyridylcarbamoyl)pyrrolidin-4-ylthio)-6-(1-hydroxyethyl)-1-methylcarbapenem-3-carboxylic acid;

(1R,5S,6S,8R,2'R,4'S)-2-(2-(2-carboxy-6-pyridylcarbamoyl)pyrrolidin-4-ylthio)-6-(1-hydroxyethyl)-1-methylcarbapenem-3-carboxylic acid;

and pharmaceutically acceptable salts and in vivo hydrolysable esters thereof.

Suitable pharmaceutically acceptable salts include acid addition salts such as hydrochloride, hydrobromide, citrate, maleate and salts formed with phosphoric and sulfuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or aminoacids, for example, lysine.

Preferred pharmaceutically acceptable salts are sodium and potassium. However, to facilitate isolation of the salt during preparation, salts which are less soluble in the chosen solvent may be preferred, whether pharmaceutically acceptable or not.

For the avoidance of doubt there may be one, two, three or four salt-forming cations depending on the number of carboxylic acid functions and valency of said cations.

In vivo hydrolysable esters are those pharmaceutically acceptable esters that hydrolyse in the human body to produce the parent hydroxy or carboxy compound. Such esters can be identified by administering, e.g. intravenously to a test animal, the compound under test and subsequently examining the test animal's body fluids. Suitable in vivo hydrolysable esters for hydroxy include acetoxy, propionyloxy, pivaloyloxy, $C_{1-4}$alkoxycarbonyloxy for example ethoxycarbonyloxy, phenylacetoxy and phthalidyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$ cycloalkoxycarbonyloxy$C_{1-6}$alkyl, for example 1-cyclohexyloxycarbonyloxyethyl; 1,3-dioxolen-2-onylmethyl esters for example 5-methyl-1,3-dioxolen-2-onylmethyl; phthalidyl esters and $C_{1-6}$alkoxycarbonyloxyethyl esters for example 1-ethoxycarbonyloxyethyl and may be formed at any carboxy group in the compounds of this invention.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids such as betamipron (also see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable composition containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by any one of examples 2 to 7.

The pharmaceutical compositions of the invention will normally be administered to man in order to combat infections caused by bacteria, in the same general manner as that employed for imipenem due allowance being made in terms of dose levels for the pharmacokinetics of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V) wherein the pyridyl ring is optionally further substituted as in formula (I):

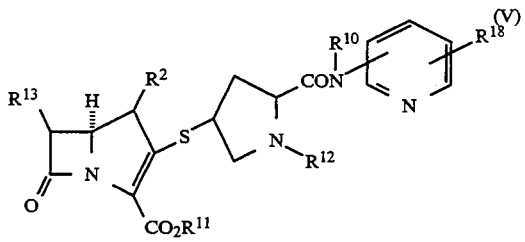

wherein $R^2$ is as hereinbefore defined; $R^{10}$ is a group $R^3$ or a amino protecting group; $R^{13}$ is a group $R^1$ protected hydroxymethyl or 1-(protected hydroxy)ethyl; $R^{11}$ is hydrogen or a carboxy protecting group; $R^{12}$ is hydrogen or an amino protecting group, $R^{18}$ is carboxy or a protected carboxy group and wherein any optional substituent on the pyridyl ring is optionally protected; and wherein at least one protecting group is present; and thereinafter if necessary;

(i) forming a pharmaceutically acceptable salt,
(ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms).

Examples of carboxy protecting groups include straight or branched chain (1–12C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, bezhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); diaryl(lower alkyl)silyl groups (e.g. t-butyldiphenylsilyl); and (2–6C)alkenyl groups (e.g. allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxycarbonyl, photolytically.

Examples of hydroxyl protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl); diaryl(lower alkyl)silyl groups (e.g. t-butyldiphenylsilyl) and aryl lower alkyl (e.g. benzyl) groups.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl); trialkylsilyl (e.g. trimethylsilyl and t-butyldimethylsilyl); diaryl(-lower alkyl)silyl group (e.g. t-butyldiphenylsilyl); alkylidene (e.g. methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

In another aspect of the present invention the compounds of the formulae (I) and (V) may be prepared by a) reacting compounds of the formulae (VI) and (VII):

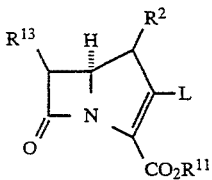

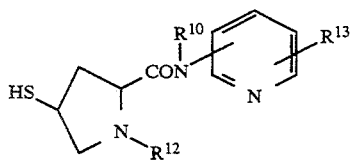

wherein $R^2$, $R^{10}$, $R^{11}$, $R^{12}$, $R^{13}$ and $R^{18}$ are as hereinbefore defined, the pyridyl ring is optionally substituted as hereinbefore defined and L is a leaving group, or b) cyclising a compound of the formula (VIII):

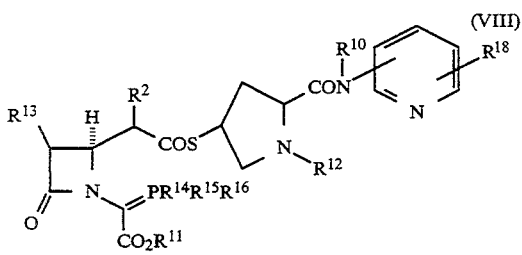

wherein $R^2$, $R^{10}$, $R^{11}$, $R^{12}$, $R^{13}$ and $R^{18}$ are as hereinbefore defined, the pyridyl ring is optionally substituted as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$-$R^{16}$ represent o-phenylenedioxy or one of $R^{14}$ to $R^{16}$ is $C_{1-4}$alkyl, alkyl, benzyl or phenyl and the other two values are independently selected from $C_{1-4}$alkyl, trifluoromethyl or phenyl wherein any phenyl group is optionally substituted with $C_{1-3}$ alkyl or $C_{1-3}$alkoxy; and wherein any functional group is optionally protected and thereinafter if necessary:

(i) removing any protecting groups;
(ii) forming a pharmaceutically acceptable salt;
(iii) esterifying to form an in vivo hydrolysable ester.

Suitably in the compound of the formula (VI), L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SOCH=CH—NH—COCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

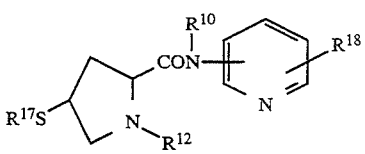

wherein $R^{10}$, $R^{12}$ and $R^{18}$ are as hereinbefore defined, the pyridyl ring is optionally substituted as hereinbefore defined and $R^{17}$ is a protecting group, for example $C_{1-6}$alkanoyl or $C_{1-6}$alkoxycarbonyl. Preferred values for $R^{17}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol, alkenol or a cyclic ether for example methanol, allyl alcohol or tetrahydrofuran.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

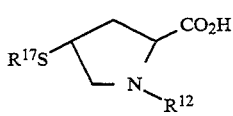

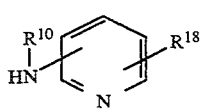

wherein $R^{10}$, $R^{12}$, $R^{17}$ and $R^{18}$ are as hereinbefore defined and the pyridyl ring is optionally substituted as hereinbefore defined. Activated derivatives of the compound of the formula (X) include acid halides, anhydrides and 'activated' esters such as 1H-benzol-1,2,3-triazol-1-yl, pentafluorophenyl and 2,4,5-trichlorophenyl esters or the benzimidazol-2-yl ester of the thiocarboxylic acid corresponding to (X). The reaction of an activated derivative of a compound of the formula (X) and a compound of the formula (XI) is performed under standard methods, for example in dichloromethane, at 0° C. in the presence of trimethylsilylchloride and diisopropylethylamine.

The compounds of the formulae (X) and (XI) are prepared by standard methods known to the skilled chemist such as the methods of the Examples hereinafter, the methods described in EP-A-126587 or by methods analogous or similar thereto.

Suitably, in the compounds of the formula (VIII), $R^{14}$, $R^{15}$ and $R^{16}$ are independently selected from $C_{1-6}$ alkoxy such as methoxy, ethoxy, isopropoxy, n-propoxy or n-butoxy; aryloxy such as optionally phenoxy; di-$C_{1-6}$alkylamino such as dimethylamino or diethylamino;

diarylamino such as diphenylamino or any two of $R^{14}-R^{16}$ represent o-phenylenedioxy. Preferably each of $R^{14}-R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

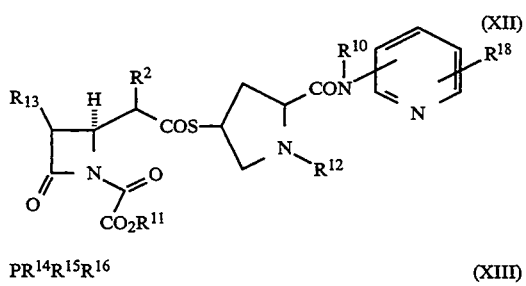

PR$^{14}$R$^{15}$R$^{16}$     (XIII)

wherein $R^2$, $R^{10}$, $R^{11}-R^{16}$, and $R^{18}$ are as hereinbefore defined and the pyridyl ring is optionally substituted as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

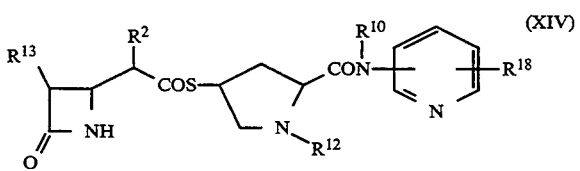

wherein $R^2$, $R^{10}$, $R^{12}$, $R^{13}$, and $R^{18}$ are as hereinbefore defined and the pyridyl ring is optionally substituted as hereinbefore defined with a compound of the formula (XV):

Cl—CO—COOR$^{11}$     (XV)

wherein $R^{11}$ is as hereinbefore defined.

The compounds of the formula (XIV) may be prepared by reacting compounds of the formulae (XVI) and (VII):

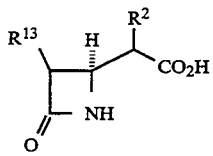

wherein $R^2$ and $R^{13}$ are as hereinbefore defined. The compounds of the formula (XVI) are known in the art and may be reacted with the compounds of the formula (VII) under conventional acylation methods known in the art.

Compounds of the formulae (VII), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and in general particularly good pharmacokinetics, especially as regards half life. In general compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| ORGANISM | MIC (µg/ml) EXAMPLE 4 |
|---|---|
| S. aureus Oxford | 0.13 |
| E. coli DC0 | 0.02 |
| P. morganii I + 001 | 0.02 |
| Enterobacter cloacae P99- | 0.02 |
| B. fragilis AMP S | 0.25 |

In the following examples, which are representative of the scope:

(a) NMR spectra were taken at 200 MHz or 400 MHz in DMSO-d$_6$/CD$_3$COOD unless otherwise stated;
(b) allyloxy means the propen-1-yloxy group —OCH$_2$CH=CH$_2$;
(c) DMF means dimethylformamide;
(d) DMSO means dimethylsulphoxide;
(e) evaporation of solvents was carried out under reduced pressure;
(f) HPLC means high pressure liquid chromatography;
(g) temperatures are given in degrees centigrade.

EXAMPLE 1

(1R,5S,6S,8R,2'S,4'S)-2-(2-(4-Carboxy-2-pyridylcarbamoyl)pyrrolidin-4-ylthio)-6-(1-hydroxyethyl)-1-methylcarbapenem-3-carboxylic acid A solution of 4-nitrobenzyl (1R,5S,6S,8R,2'S,4'S)-2-(1-(4-nitrobenzyloxycarbamoyl)-2-(4-carboxy-2-pyridylcarbamoyl)pyrrolidin-4-ylthio)-6-(1-hydroxyethyl)-1-methylcarbapenem-3-carboxylate (695 mg, 0.88 mmol) in a mixture of methanol/ethyl acetate ($\frac{1}{4}$) (20 ml), water (20 ml) and KHCO$_3$ (200 mg, 2 mmol) was hydrogenated over Pd/carbon (10%), (400 mg). The reaction was followed by HPLC. The residue is purified by subjecting to preparative HPLC (Nucleosil C-18) after filtration of the solid and concentration, to give the title compound (76 mg, 16%).

NMR: δ1.16 (m, 6H); 1.75 (m, 1H); 2.6–2.74 (m, 2H); 3.2 (dd, 1H) 3.3–3.5 (m, 2H); 3.63 (m, 1H); 3.96 (m, 2H); 4.15 (m, 1H); 7.5 (d, 1H); 8.37 (d, 1H); 8.53 (s, 1H).

The starting material was prepared as follows:

(2S,4S)-1-(4-Nitrobenzyloxycarbonyl)-4-acetylthiocarboxypyrrolidine (1.5 g, 4 mmol) was treated at ambient temperature, for 5 hours, with thionyl chloride (12 ml) and a catalytic amount of DMF (15 mg). The solvent was evaporated, the residue taken up in CH$_2$Cl$_2$, evaporated, dried under reduced pressure for 1 hour and solubilized in CH$_2$Cl$_2$ (10 ml). This solution was added to a cold (0° C.) solution of 2-amino-4-carboxypyridine (560 mg, 4 mmol) diisopropylethylamine (2.12 ml, 12 mmol) and trimethylsilylchloride (1 ml, 12 mmol) in dry CH$_2$Cl$_2$. After 12 hours at ambient temperature, the solvent was evaporated, the residue purified by subjecting to chromatography on HP20SS resin, (eluant: CH$_3$CN/H$_2$O) to give (2S,4S)-1-(4-nitrobenzyloxycarbonyl)-2-(4-carboxy-2-pyridylcarbamoyl)pyrrolidin-4-ylthioacetate (650 mg, 32.5%).

NMR: δ1.9 (m, 1H); 2.32 (s, 3H); 2.83 (m, 1H); 3.36 (m, 1H); 4.0 (m, 2H); 4.64 (s, 1H); 4.9–5.35 (m, 2H); 7.4–7.7 (m, 3H); 7.92 (s, 1H); 8.2 (s, 1H); 8.47 (m, 2H).

(2S,4S)-1-(4-Nitrobenzyloxycarbonyl)-2-(4-carboxy-2-pyridylcarbamoyl)pyrrolidin-4-ylthioacetate (488 mg, 1 mmol) in methanol (20 ml) was treated with a 1M aqueous solution of NaOH (2.5 ml, 2.5 mmol) under argon, at 0° C. The reaction was followed by HPLC. After 1 hour the reaction mixture was acidified (at pH 6.5, 0° C. with 6M HCl), the solvent evaporated and dried under reduced pressure for 1 hour. The resulting crude thiol was solubilized in DMF (5 ml) and added to a cold (0° C.) solution of 4-nitrobenzyl (1R,5R,6S,8R)-6-(1-hydroxy)-1-methyl-2-diphenylphosphoryloxycarbapenem-3-carboxylate (499 mg, 0.84 mmol) in DMF (5 ml). This solution was treated successively with diisopropylethylamine (350 μl, 1 mmol) tri-n-butylphosphine (250 μl, 1 mmol) and water (20 μl, 1 mmol), and stirred at ambient temperature overnight. The crude reaction mixture was purified by subjecting to chromatography on a HP20SS column, to give 4-nitrobenzyl (1R,5R,6S,8R,2'S,4'S)-2-(1-(4-nitrobenzyloxycarbonyl)-2-(4-carboxy-2-pyridylcarbamoyl)pyrrolidin-4-ylthio)-6-(1-hydroxyethyl-1-methylcarbapenem-3-carboxylate (695 mg, 88%) (eluting with CH$_3$CN/H$_2$O gradient of CH$_3$CN.)

NMR: δ1.4 (m, 6H); 1.9 (m, 1H); 2.83 (m, 1H); 3.3–3.5 (m, 2H); 3.6 (m, 1H); 3.9–4.1 (m, 2H); 4.1–4.3 (m, 2H); 3.6 (m, 1H); 3.6 (m, 1H); 5.0–5.5 (m, 4H); 7.4–7.8 (m, 5H); 7.9 (d, 1H); 8.2 (m, 3H); 8.4–8.6 (m, 2H).

Example 2

(1R,5S,6S,8R,2'S,4'S)-2-(2-(3-Carboxy-5-pyridylcarbamoyl)-pyrrolidin-4-ylthio)-6-(1-hydroxyethyl)-1-methylcarbapenem-3-carboxylic acid.

The title compound was prepared from the corresponding 4-nitrobenzyl protected compound using a similar method to that of example 1.

NMR: δ0.85 (m, 6H); 1.28 (m, 4H); 1.3–1.5 (m, 4H); 2.63 (m, 1H); 2.8 (m, 1H); 3.2 (dd, 1H); 3.4 (m, 2H); 3.65 (m, 1H); 3.95 (m, 2H); 4.15 (m, 1H); 8.58 (m, 1H); 8.76 (s, 1H); 8.93 (m, 1H).

(2S,4S)-1-(4-Nitrobenzyloxycarbonyl)-2-(3-carboxy-5-pyridylcarbamoyl)pyrrolidin-4-ylthioacetate was prepared using a similar method to that of example 1, except using 5-amino-3-carboxypyridine acid in place of 2-amino-4-carboxypyridine.

NMR: δ1.9 (m, 1H); 2.32 (s, 3H); 2.83 (m, 1H); 3.36 (m, 1H); 4.0 (m, 2H); 4.5 (m, 1H); 5.0'5.35 (m, 2H); 7.5 (d, 1H); 7.7 (d, 1H); 7.95 (d, 1H); 8.25 (d, 1H); 8.5–9.0 (m, 3H).

Allyl (1R,5R,6S,8R,2'S,4'S)-2-(1-(4-nitrobenzyloxycarbonyl)-2-(3-carboxy-5-pyridylcarbamoyl)pyrrolidin-4-ylthio)-6-(1-hydroxyethyl)-1-methylcarbapenem-3-carboxylate was prepared using a similar method to that of example 1, except using allyl (1R,5R,6S,8R)-6-(1-hydroxyethyl)-1-methyl-2-diphenylphosphorylcarbapenem-3-carboxylate as the carbapenem precursor, and the thioacetate product of the previous step in place of (2S,4S)-1-(4-nitrobenzyloxycarbonyl)-2-(4-carboxy-2-pyridylcarbamoylpyrrolidin-4-ylthioacetate.

NMR: δ1.27 (m, 6H); 1.95 (m, 1H); 2.8 (m, 1H); 3.26 (dd, 1H); 3.38 (m, 1H); 3.55 (m, 1H); 3.98 (m, 2H); 4.1 (m, 1H); 4.25 (m, 1H); 4.4–4.75 (m, 3H); 5.5–5.45 (m, 4H); 5.88 (m, 1H).

Allyl (1R,5R,6S,8R,2'S,4'S) 2-(1-(4-nitrobenzyloxycarbonyl)-2-(3-carboxy-5-pyridylcarbamoyl)pyrrolidin-4-ylthio)-6-(1-hydroxyethyl)-1-methylcarbapenem-3-carboxylate (450 mg, 0.65 mmol) in THF (25 ml) was treated at ambient temperature with triphenylphosphine (17 mg, 0.065 mmol), potassium hexanoate 0.46M in ethyl acetate (3.4 ml, 1.55 mmol) and Pd(PPh$_3$)$_4$ (25 mg, 0.02 mmol) for 1 hour. The mixture was diluted with ethyl acetate (25 ml), the solid filtered, washed with ethyl acetate and dried (395 mg, 83.5%). This compound as used in the following step without further purification.

Example 3

(1R,5S,6S,8R,2'S,4'S)-2-(2-(3-Carboxy-2-pyridylcarbamoyl) pyrrolidin-4-ylthio)-6-(1-hydroxyethyl)-1-methylcarbapenem-3-carboxylic acid.

The title compound was prepared from the corresponding 4-nitrobenzyl protected compound, using a similar method to that of example 1.

NMR: δ1.15 (2d, 6H), 1.74 (m, 1H); 2.7–2.95 (m, 2H); 3.2 (dd, 1H); 3.39 (m, 1H); 3.51 (m, 1H); 3.71 (m, 1H); 3.96 (q, 1H); 4.15 (dd, 1H); 4.39 (m, 1H); 7.11 (m, 1H); 8.23–8.38 (m, 2H).

The starting material was prepared as follows:

(2S,4S) 1-(4-Nitrobenzyloxycarbonyl)-2-(3-carboxypyridylcarbamoyl)pyrrolidin-4-ylthioacetate was prepared using a similar method of that of example 1, except using 2-amino-3-carboxypyridine in place of 2-amino-4-carboxypyridine.

NMR: $\delta$2.05 (m, 1H); 2.3 (s, 3H); 2.85 (m, 1H); 3.35 (m, 1H); 3.8–4.25 (m, 2H); 4.74 (dd, 1H); 5.16 (m, 2H); 7.18 (dd, 1H); 7.5 (d, 2H); 8.04 (d, 2H); 8.23 (dd, 1H); 8.46 (dd, 1H).

Allyl (1R,5R,6S,8R,2'S,4'S) 2-(1-(4-nitrobenzyloxycarbonyl)-2-(3-carboxy-2-pyridylcarbamoylpyrrolidin-4-ylthio)-6-(1-hydroxyethyl)-1-methylcarbapenem-3-carboxylate (diisopropylethylamine salt) was prepared using a similar method to that of example 2 from the thioacetate product of the previous step.

NMR: $\delta$1.06–1.35 (m, 21H); 2.0 (m, 1H); 2.88 (m, 1H); 3.12 (q, 2H; 3.25 (dd, 1H); 3.35 (m, 1H); 3.42–3.68 (m, 3H); 3.9–4.05 (m, 2H); 4.1–4.3 (m, 2H); 4.46–4.8 (m, 3H); 5.0–5.42 (m, 4H); 5.85 (m, 1H); 7.15 (dd, 1H); 7.45 (d, 1H); 7.68 (d, 1H); 7.93 (d, 1H); 8.15–8.31 (m, 2H); 8.4 (m, 1H).

(1R,5R,6S,8R,2'S,4'S) 2-(1-(4-Nitrobenzyloxycarbonyl)-2-(3-carboxy-2-pyridylcarbamoyl)pyrrolidin-4-ylthio)-6-(1-hydroxyethyl)-1-methylcarbapenem-3-carboxylic acid was prepared from the allyl protected compound of the last step using a similar method to that of example 2.

Example 4

(1R,5R,6S,8S,2'S,4'S)-2-(2-(5-Carboxy-2-pyridylcarbamoyl)pyrrolidin-4-ylthio)-6-(1-hydroxyethyl)-1-methylcarbapenem-3-carboxylic acid.

The title compound prepared from the corresponding 4-nitrobenzyl protected compound, using a similar method to that of example 1.

NMR: $\delta$1.15 (2d, 6H); 1.75 (m, 1H); 2.55–2.79 (m, 2H); 3.18 (dd, 1H); 3.3–3.5 (m, 2H); 3.63 (m, 1H); 3.9–4.07 (m, 2H); 4.14 (dd, 1H): 8.17 (d, 1H); 8.28 (dd, 1H); 8.82 (m, 1H).

The starting material was prepared as follows:

(2S,4S)-1-(4-Nitrobenzyloxycarbonyl)-2-(5-carboxy-2-pyridylcarbamoyl)pyrrolidin-4-ylthioacetate was prepared using a similar method to that of example 1, except using 2-amino-5-carboxypyridine in place of 2-amino-4-carboxypyridine.

NMR: $\delta$2.05 (m, 1H); 2.3 (s, 3H); 2.85 (m, 1H); 3.37 (m, 1H); 3.8–4.25 (m, 2H); 4.66 (m, 1H); 5.18 (m, 2H); 7.52 (d, 2H); 7.88–8.33 (m, 4H); 8.78 (m, 1H).

Allyl (1R,5R,6S,8R,2'S,4'S) 2-(1-nitrobenzyloxycarbonyl)-2-(5-carboxy-2-pyridylcarbamoyl)pyrrolidin-4-ylthio)-6-(1-hydroxyethyl)-1-methylcarbapenem-3-carboxylate was prepared from the thioacetate product of the previous step using a similar method to that of example 2.

NHR: $\delta$1.15 (2d, 6H); 1.9 (m, 1H); 2.83 (m, 1H); 3.22–3.44 (m, 2H); 3.58 (q, 1H); 3.86–4.06 (m, 2H); 4.1–4.3 (m, 2H); 4.55–4.8 (m, 3H); 5.16–5.48 (m, 4H); 5.92 (m, 1H); 7.46 (d, 1H); 7.67 (d, 1H); 7.92 (d, 1H); 8.08–8.32 (m, 3H); 8.83 (d, 1H).

(1R,5R,6S,2'S,4'S) 2-(1-(4-Nitrobenzyloxycarbonyl)-2-(5-carboxy-2-pyridylcarbamoyl)pyrrolidin-4-ylthio)-6-(1-hydroxyethyl)-1-methylcarbapenem-3-carboxylic acid was prepared from the product of the previous step using a similar method to that of example 2.

Example 5

(1R,5S,6S,8R,2'S,4'S)-2-(2-(2-Carboxy-4-pyridylcarbamoyl)pyrrolidin-4-ylthio)-6-(1-hydroxyethyl)-1-methylcarbapenem-3-carboxylic acid (2K+).

A solution of (1R,5S,6S,2'S,4'S)-2-(1-(4-nitrobenzyloxycarbonyl)-2-(2-carboxy-4-pyridylcarbamoyl)pyrrolidin-4-ylthio)-6-(1-hydroxyethyl)-1-methylcarbapenem-3-carboxylic acid (2K+) (0.4 g, 0.55 mmol) in water (15 ml) was hydrogenated at atmospheric pressure in the presence of 10% Pd/C. (0.2 g) and potassium bicarbonate (55 mg, 0.55 mmol). The progress of the reaction was followed by analytical HPLC. The catalyst was removed by filtration, the filtrate purified by preparative HPLC on $C_{18}$ Nucleosil, eluting with water. The product was recovered and freeze dried (0.1 g, 33%).

NMR (DMSO+CD$_3$COOD): $\delta$1.16 (m, 6H); 1.76 (m, 1H); 2.62 (m, 1H); 2.77 (m, 1H); 3.19 (dd, 1H); 3.37 (m, 2H); 3.64 (m, 1H); 3.96 (m, 2H); 4.15 (dd, 1H); 7.88 (dd, 1H); 8.34 (d, 1H); 8.51 (d, 1H).

The starting material was prepared as follows:

A solution of 2-carboxy-4-nitropyridine N-oxide (0.5 g, 27 mmol) (E. Prafft et al., J. Prakt. Chem. 1961, 13, 58) in acetic acid (20 ml) was hydrogenated under pressure (70 psi) in the presence of Pd/C. (10%) (0.25 g) at ambient temperature for 2 hours. The catalyst was removed by filtration, and the filtrate evaporated to give 2-carboxy-4-aminopyridine as an off-white solid which was dried in a dessicator (300 mg, 80%).

NMR (D$_2$O): $\delta$6.75 (d, 1H); 7.17 (s, 1H); 8.11 (d, 1H).

(2S,4S)-1-(4-Nitrobenzyloxycarbonyl)-4-acetylthio-2-carboxypyrrolidine (1.5 g, 4 mmol) in CH$_2$Cl$_2$ (10 ml) was treated at ambient temperature, for 12 hours, with thionyl chloride (1.4 ml, 19 mmol) and a catalytic amount of DMF (20 $\mu$). The solution was then evaporated, and the residue dried under vacuum for two hours, solubilized in CH$_2$Cl$_2$ (10 ml) and added to a solution of 2-carboxy-4-aminopyridine (0.887 g, 4.5 mmol), diisopropylethylamine (35 ml, 20 mnol) and trimethylsilylchloride (3 ml, 25 mmol) in CH$_2$Cl$_2$ (20 ml), at 0° C. The reaction was monitored by HPLC. After 12 hours at ambient temperature, the mixture was evaporated and the residue purified by chromatography on a HP20SS column, eluting with CH$_3$CN/H$_2$O/AcOH (1:1:1/100). The required fractions were collected and freeze dried to give (2S,4S)-1-(4-nitrobenzyloxycarbonyl)-2-(2-carboxy-4-pyridylcarbamoyl)pyrrolidin-4-ylthioacetate (1.06 g, 53%).

NMR (DMSO+CD$_3$COOD): $\delta$2.0 (m, 1H); 2.33 (s, 3H); 2.83 (m, 1H), 3.4 (m, 1H); 4.1 (m, 2H); 4.6 (m, 1H); 5.2 (m, 2H); 7.5 (m, 1H); 7.67 (m, 1H); 8.02 (m, 1H); 8.15 (m, 2H); 8.5–8.8 (m, 2H).

(2S,4S)-1-(4-Nitrobenzyloxycarbonyl)-2-(2-carboxy-4-pyridylcarbamoyl)pyrrolidin-4-ylthioacetate (0.448 g, 1 mmol) in MeOH (20 ml) was treated with 1N NaOH (2.5 ml, 2.5 mmol), added drop by drop, at ambient temperature. After 30 minutes the mixture was acidified with 6N HCl, at 0° C., and the solvent evaporated. The residue was solublized in DMF (5 ml) and added to a solution of allyl (1R,5R,6S,8R)-6-(1-hydroxyethyl)-1-methyl-2-diphenylphosphoryloxycarbapenem-3-carboxylate (0.499 g, 1 mmol), in DMF (5 ml), in the presence of N,N'-diisopropylethylamine (0.35 ml, 2 mmol), water (18 $\mu$l, 1, 1 mmol) and n-tributylphosphine (0.25 ml, 1 mmol). The mixture was left for 12 hours at ambient temperature. The crude reaction mixture was poured onto a HP20SS column, and eluted with CH₃CN/H₂O (gradient of CH₃CN) to give allyl (1R,5R,6S,8R,2'S,4'S)-2-(1-(4-nitrobenzyloxycarbonyl)-2-(2-carboxy-4-pyridylcarbamoyl)pyrrolidin-4-ylthio)-6-(1-hydroxyethyl)-1-methylcarbapenem-3-carboxylate (0.4 g, 57.5%).

NMR: (DMSO+CD₃COOD): δ1.26 (m, 6H); 1.95 (m, 1H); 2.82 (m, 1H); 3.27 (dd, 1H); 3.4 (m, 1H); 3.6 (m, 1H); 3.98 (m, 2H); 4.13 (m, 1H); 4.25 (m, 1H); 4.44–4.7 (m, 3H); 5.05–5.42 (m, 4H); 5.88 (m, 1H); 7.47 (m, 1H); 7.67 (m, 1H); 7.86–7.96 (m, 2H); 8.23–8.30 (m, 2H); 8.54 (m, 1H).

Allyl (1R,5R,6S,8R,2'S,4'S)-2-(1-(4-nitrobenzyloxycarbonyl)-2-(2-carboxy-4-pyridylcarbamoyl)pyrrolidin-4-ylthio)-6-(1-hydroxyethyl)-1-methylcarbapenem-3-carboxylate (0.4 g, 0.575 mmol), in THF (20 ml), was treated successively with PPh₃ (15 mg, 0.05 mmol), potassium hexanoate in ethyl acetate (3.6 ml, 1.43 mmol, 0.47M) and Pd(PPh₃)₄ (20 mg, 0.017 mmol). The reaction was followed by HPLC. After 15 minutes, the reaction mixture was diluted with ethyl acetate (20 ml) and the precipitate recovered by filtration and dried to give (1R,5R,6S,8R,2'S,4'S)-2-(1-(4-nitrobenzyloxycarbonyl-2-(2-carboxy-4pyridylcarbamoyl)pyrrolidin-4-ylthio)-6-(1-hydroxyethyl)-1-methylcarbapenem-3-carboxylic acid (2K+) (0.4 g, 95%).

NMR (DMSO+CD₃COOD): δ1.15 (m, 6H); 1.95 (m, 1H); 2.8 (m, 1H); 3.2 (dd, 1H); 3.4 (m, 2H); 3.8–4.2 (m, 4H); 4.5 (m, 1H); 5.0–5.3 (m, 2H); 7.47 (m, 1H); 7.67 (m, 1H); 7.75–8.00 (m, 2H); 8.25 (m, 2H); 8.5 (m, 1H).

Example 6

(1R,5S,6S,8R,2'S,4'S)2-(2-Carboxy-6-pyridylcarbamoyl)pyrrolidin-4-ylthio)-6-(1-hydroxyethyl)-1-methylcarbapenem-3-carboxylic acid (2K+).

The deprotection of (1R,5S,6S,2'S,4'S)-2-(1-(4-nitrobenzyloxycarbonyl)-2-(2-carboxy-6-pyridylcarbamoyl)pyrrolidin-4-ylthio)-6-(1-hydroxyethyl)-1-methylcarbapenem-3-carboxylic acid (2K+) was carried out using a similar method to that described in Example 5.

NMR (DHSO-d₆ +CD₃COOD) δ1.15 (m, 6H); 1.85 (m, 1H); 2.78 (m,H); 2.93 (m, 1H); 3.19 (dd, 1H); 3.37 (dt, 1H), 3.56 (m, 1H); 3.76 (m, 1H); 3.96 (dq; 1H); 4.18 (m, 2H); 7.76 (d, 1H); 7.92 (m, 1H); 8.24 (d, 1H).

The starting material was prepared as follows:

A solution of 2-carboxy-6-aminopyridine (0.4 g, 2.89 mmol) in DMF (4 ml) was treated successively with allylbromide (0.37 ml, 4.33 mmol) and potassium carbonate (0.48 g, 3.47 mmol). The mixture was stirred for one hour at ambient temperature and kept for two hours at 60° C. The reaction mixture was then cooled, poured on ice, extracted with ethyl acetate, washed with water and dried over MgSO₄. The required product was obtained by silica gel chromatography, eluting with petroleum ether/ether (1:1), to give 2-allyloxycarbonyl-6-aminopyridine (295 mg, 57%).

NMR (CDCl₃): δ4.79 (m, 2H); 4.87 (m, 2H); 5.29 (m, 1H); 5.42 m, 1H); 6.05 (m, 1H); 6.67 (m, 1H);; 7.5 (m, 2H).

(2S,4S)-1-(4-Nitrobenzyloxycarbonyl)-4-acetylthio-2-carboxypyrrolidine (0.62 g, 1.69 mmol) in dry CH₂Cl₂ (5 ml) was treated with thionyl chloride (0.6 ml) and a catalytic amount of DMF (10 μl) for 12 hours, at ambient temperature. The solution was then evaporated, and the residue dried under vacuum for two hours. The residue was solubilized in CH₂Cl₂ (4 ml) and added to a solution of 2-allyloxycarbonyl-6-aminopyridine (0.275 g, 1.55 mmol) and diisopropylethylamine (0.27 ml, 1.55 mmol) in CH₂Cl₂ (4 ml), at 0° C. The mixture was stirred at ambient temperature for two hours, the solvent evaporated, and the residue purified by silica gel chromatography, eluting with CH₂Cl₂/ether (9:1), to give (2S,4S)-1-(4-nitrobenzyloxycarbonyl)-2-(2-allyloxycarbonyl-6-pyridylcarbamoyl)-pyrrolidin-4-ylthioacetate (0.69 g, 85%).

NMR (CDCl₃): δ2.28 (m, 1H); 2.31 (s, 3H); 2.76 (m, 1H); 3.45 (m, 1H); 4.01 (m, 1H); 4.17 (m, 1H); 4.47 (m, 1H); 4.88 (m, 2H); 5.37 (m, 4H); 6.04 (m, 1H); 7.47 (m, 1H); 7.85 (m, 2H); 7.9–8.45 (m, 4H).

(2S,4S)-1-(4-Nitrobenzyloxycarbonyl)-2-(2-allyloxycarbonyl-6-pyridylcarbamoyl)pyrrolidin-4-ylthioacetate (0.69 g, 1.3 mmol) in a mixture of EtOH (7.5 ml) and CH₂Cl₂ (2 ml) was treated with a solution of methylamine in EtOH (2.6 mmol) for 1 hour, at 0° C. The mixture was concentrated, the residue solublized in CH₃CN (10 ml) and added to a solution of allyl (1R,5R,6S,8R)-6-(1-hydroxyethyl)-1-methyl-2-diphenylphosphoryloxycarbapenem-3-carboxylate (0.65 g, 1.3 mmol) in acetonitrile (5 ml). This mixture was then treated successively with N,N'-diisopropylethylamine (0.45 ml, 2.6 mmol), water (25 μl, 1.3 mmol) and n-tributylphosphine (0.32 ml, 1.3 mmol). The mixture was stirred for 3 hours at ambient temperature, evaporated to dryness and the residue purified by silica gel chromatography, eluting with EtOAc, to give allyl (1R,5R,6S,8R,2'S,4'S)-2-(1-(4-nitrobenzyloxycarbonyl)-2-(2-allyloxycarbonyl-6-pyridylcarbamoyl)pyrrolidin-4-ylthio)-6-(1-hydroxyethyl)-1-methylcarbapenem-3-carboxylate (0.5 g, 52%).

NMR (DMSO-d₆): δ1.15 (m, 6H); 1.86 (m, 1H); 2.81 (m, 1H); 3.3 (m, 2H); 3.58 (m, 1H); 3.94 (m, 2H); 4.1–4.3 (m, 2H); 4.55–4.9 (m, 5H); 4.95–5.5 (m, 6H); 5.90 (m, 1H); 6.05 (m, 1H); 7.46–7.7 (m, 2H); 7.75–8.1 (m, 3H); 8.2–8.35 (m, 2H).

The allyl group was removed from allyl (1R,5R,6S,8R,2'S,4'S)-2-(1-(4-nitrobenzyloxycarbonyl)-2-(2-allyloxycarbonyl-6-pyridylcarbamoyl)pyrrolidin-4-ylthio)-6-(hydroxyethyl)-1-methylcarbapenem-3-carboxylate using a similar method to that described in Example 5, to give (1R,5R,6S,8R,2'S,4'S)-2-(1-(4-nitrobenzyloxycarbonyl-2-(2-carboxy-6-pyridylcarbamoyl)pyrrolidin-4-ylthio)-6-(1-hydroxyethyl)-1-methylcarbapenem-3-carboxylic acid (2K+).

Example 7

(1R,5S,6S,8R,2'R,4'S)-2-(2-Carboxy-6-pyridylcarbamoyl)pyrrolidin-4-ylthio)-6-(1hydroxyethyl)-1-methylcarbapenem-3-carboxylic acid (2K+).

The deprotection of (1R,5S,6S,8R,2'R,4'S)-2-(1-(4-nitrobenzyloxycarbonyl)-2-(2-carboxy-6-pyridylcarbamoyl)pyrrolidin-4-ylthio)-6-(1-hydroxyethyl)-1-methylcarbapenem-3-carboxylic acid (2K+) was carried out using a similar method to that described in Example 5, to give the title compound.

NMR (DMSO-d₆): δ1.15 (m, 6H); 2.08 (m, 1H); 2.35 (m, 1H); 2.95 (m, 1H); 3.17 (dd, 1H); 3.34 (m, 2H); 3.76 (m, 1H); 3.95 (m, 1H); 4.14 (m, 2H); 7.73 (m, 1H); 7.91 (m, 1H); 8.24 (m, 1H).

The starting material was prepared as follows:

(2R,4S)-1-(4-Nitrobenzyloxycarbonyl)-4-acetylthio-2-carboxypyrrolidine (1.5 g, 4 mmol) in dry CH₂Cl₂ was treated with thionyl chloride (1.4 ml, 19 mmol) and a catalytic amount of DMF(20 μl) for 12 hours at ambient temperature. The solution was evaporated, and the residue dried under vacuum for 2 hours. The residue was solubilized in CH$_2$Cl$_2$ (10 ml) and added to a solution of 2-carboxy-6-aminopyridine (G. Ferrari et al., Farmaco (pavia) Ed. Sci. 1959, 14, 594. CA 53, 7162b) (560 mg, 4 mmol) in CH$_2$Cl$_2$ (20 ml), diisopropylethylamine (3.5 ml, 20 mmol) and trimethylsilylchloride (3 ml, 24 mmol), at 0° C. The mixture was stirred at ambient temperature for 4 hours, the solvent evaporated and the residue purified by HP20SS chromatography, eluanting with CH$_3$CN/H$_2$O/AcOH (1:1:1/100) to give (2R,4S)-1-(4-nitrobenzyloxycarbonyl)-2-(2-carboxy-6-pyridylcarbamoyl)pyrrolidin-4-ylthioacetate (1 g, 50%).

(2R,4S)-1-(4-Nitrobenzyloxycarbonyl)-2-(2-carboxy-6-pyridylcarbamoyl)pyrrolidin-4-ylthioacetate was reacted with allyl (1R,5R,6S,8R)-6-(1-hydroxyethyl)-1-methyl-2-diphenylphosphoryloxycarbapenem-3-carboxylate using a similar method to that described in Example 5, to give allyl (1R,5R,6S,8R,2'R,4'S)-2-(1-(4-nitrobenzyloxycarbonyl)-2-(2-carboxy-6-pyridylcarbamoyl)pyrrolidin-4-ylthio)-6-(1-hydroxyethyl)-1-methylcarbapenem-3-carboxylate.

The allyl protecting group was removed from allyl (1R,5R,6S,8R,2'R,4'S)-2-(1-(4-nitrobenzyloxycarbonyl)-2-(2-carboxy-6-pyridylcarbamoyl)pyrrolidin-4-ylthio)-6-(1-hydroxyethyl)-1-methylcarbapenem-3-carboxylate using a similar method to that described in Example 5, to give (1R,5R,6S,8R,2'R,4'S)-2-(1-(4-nitrobenzyloxycarbonyl)-2-(2-carboxy-6-pyridylcarbamoyl)pyrrolidin-4-ylthio)-6-(1-hydroxyethyl)-1-methylcarbapenem-3-carboxylic acid (2K+).

I claim:

1. A compound of the formula (I):

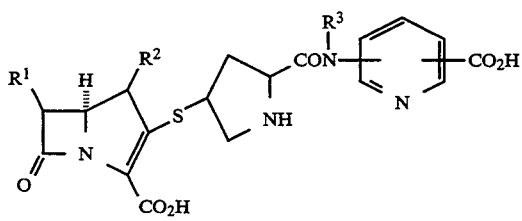

wherein:

R$^1$ is 1-hydroxyethyl, 1-fluoroethyl or hydroxymethyl;

R$^2$ is hydrogen or C$_{1-4}$alkyl;

R$^3$ is hydrogen or C$_{1-4}$alkyl;

and the pyridyl group is bonded to the nitrogen of the linking carbamoyl group by a carbon atom, is substituted with the carboxy group on a carbon atom, and is optionally substituted on one or two pyridyl ring carbon atoms by a substituent selected from halo, cyano, C$_{1-4}$alkyl, nitro, hydroxy, carboxy, C$_{1-4}$alkoxy, trifluoromethyl, C$_{1-4}$alkoxycarbonyl, amino, C$_{1-4}$alkylamino, di-C$_{1-4}$alkylamino, C$_{1-4}$alkylS(O)$_n$- (wherein n is 0-2), C$_{1-4}$alkylamino, C$_{1-4}$alkanoyl(N-C$_{1-4}$alkyl)amino, carbamoyl, C$_{1-4}$alkylcarbamoyl and di-C$_{1-4}$alkylcarbamoyl:

or a pharmaceutically acceptable salt or in vivo hydrolysable ester thereof.

2. The compound according to claim 1 wherein R$^1$ is 1-hydroxyethyl and R$^2$ is methyl.

3. The compound according to either claim 1 or claim 2 of the formula (IV):

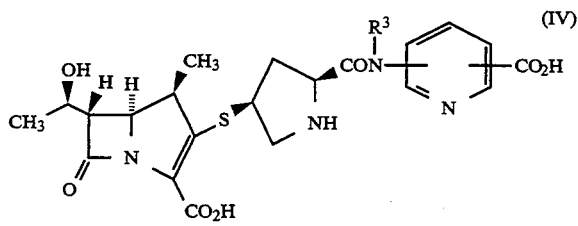

wherein R$^3$ and optional substituents on the pyridyl ring are as defined in claim 1.

4. The compound according to either claim 1 or claim 2 of the formula (IVA):

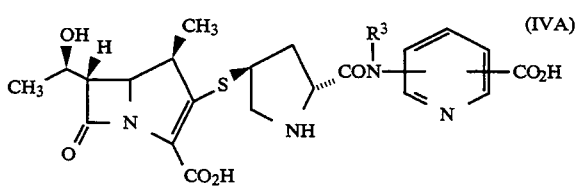

wherein R$^3$ and optional substituents on the pyridyl ring are as defined in claim 1.

5. The compound according to claim 3 wherein the optional substituents on pyridyl ring are selected from halo, cyano, C$_{1-4}$alkyl, nitro, hydroxy, carboxy, C$_{1-4}$alkoxy, carbamoyl, amino and trifluoromethyl.

6. The compound according to claim 1 which is (1R,5S,6S,8R,2'S,4'S)-2-(2-(4-carboxy-2-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-5-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-pyridylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6-pyridylcarbamoyl)pyrrolidin-4-ylthio)-6-(1-hydroxyethyl)-1-methylcarbapenem-3-carboxylic acid;

(1R,5S,6S,8R,2'R,4'S)-2-(2-(2-carboxy-6-pyridylcarbamoyl)pyrrolidin-4-ylthio)-6-(1-hydroxyethyl)-1-methylcarbapenem-3-carboxylic acid;

and pharmaceutically acceptable salts thereof.

7. A pharmaceutical composition which comprises a pharmaceutically effective amount of a compound according to claim 1 and a pharmaceutically acceptable carrier.

8. A method of treatment of a bacterial infection by administering an antibacterially effective amount of a compound according to claim 1 to a patient in need thereof.

* * * * *